US006446011B1

(12) United States Patent
Floratos et al.

(10) Patent No.: US 6,446,011 B1
(45) Date of Patent: Sep. 3, 2002

(54) TANDEM REPEAT DETECTION USING PATTERN DISCOVERY

(75) Inventors: Aris Floratos; Isidore Rigoutsos, both of Astoria; Gustavo A. Stolovitzky, Bronx, all of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/528,601

(22) Filed: Mar. 20, 2000

Related U.S. Application Data

(60) Provisional application No. 60/126,314, filed on Mar. 26, 1999.

(51) Int. Cl.[7] ........................... G01N 33/48; G06F 17/21
(52) U.S. Cl. ............................ 702/19; 702/20; 700/30; 707/6; 704/10; 704/243; 435/6
(58) Field of Search ..................... 702/19, 20; 700/30; 707/6; 435/6; 704/10, 243

(56) References Cited

U.S. PATENT DOCUMENTS

| | | | | |
|---|---|---|---|---|
| 5,809,499 A | * | 9/1998 | Wong et al. ................... | 707/6 |
| 5,819,266 A | * | 10/1998 | Agrawal et al. ............... | 707/6 |
| 5,977,890 A | | 11/1999 | Rigoutsos et al. | |
| 6,092,065 A | * | 7/2000 | Floratos et al. ................ | 707/6 |
| 6,108,666 A | * | 8/2000 | Floratos et al. ............. | 707/104 |

OTHER PUBLICATIONS

Benson, "Tandem repeats finder: a program to analyze DNA sequences", Nucleric Acids Research, 1999 vol. 27 No. 2, pp. 573–580.*
Lawrence et al., "Detecting Subtle Sequence Signals: A Gibbs Sampling Strategy for Multiple Alignment", Science vol. 262 Oct. 1993 pp. 208–214.*

G. Benson et al., "Tandem Repeats Finder: A Program to Analyze DNA Sequences," Nucleic Acids Research, vol. 27, No. 2, Oxford University Press, pp. 573–580, 1999.
K. Kawakami et al., "Polymorphic Tandem Repeats in the Thymidylate Synthase Gene is Associated with its Protein Expression in Human Gastrointestinal Cancers," Anticancer Research 19:3249–3252, 1999.
G. Stolovitsky et al., "Research Report: Tandem Repeat Detection Using Pattern Discovery with Applications to the Identification of Yeast Satellites," RC21508(96944), pp. 1–52, May 1999.
G. Benson, "An Algorithm for Finding Tandem Repeats of Unspecified Pattern Size," S. Istrail et al. (editors), Proc. 2nd Annual ACM International Conference on Computational Molecular Biology, RECOMB 98, pp. 1–11, 1998.
R. Rigoutsos et al., "Combinatorial Pattern Discovery in Biological Sequences: the TEIRESIAS Algorithm," Bioinformatics, vol. 14, No. 1, pp. 55–67, 1998.
I. Rigoutsos et al., "Motif Discovery Without Alignment or Enumeration," Proc. 2nd Annual ACM International Conference on Computational Molecular Biology, RECOMB 98, pp. 221–227, 1998.

(List continued on next page.)

Primary Examiner—Mary K. Zeman
(74) Attorney, Agent, or Firm—Casey P. August; Ryan, Mason & Lewis, LLP

(57) ABSTRACT

An algorithm which detects tandem repeats (TR) is provided. In an illustrative embodiment, a set of repeating units contained in an input sequence is identified, wherein each given repeating unit satisfies at least the following conditions: (a) a first measure of similarity between adjacent repeating units in the set is greater than a first user defined threshold, and (b) the given repeating unit includes at least one unit having a second measure of similarity with any other unit in the set that is a greater than a second user defined threshold. The method then provides for reporting positions in the input sequence that are covered by the set of repeating units.

24 Claims, 7 Drawing Sheets

OTHER PUBLICATIONS

M.–F. Sagot et al., "Identifying Satellites in Nucleic Acid Sequences," Proc. 2nd Annual ACM International Conference on Computational Molecular Biology, RECOMB 98, pp. 234–242, 1998.

K. Inman et al., An Introduction to Forensic DNA Analysis, CRC Press, Boca Raton, FL, pp. 29–35, 1997.

B Lewin, "Genes VI," Oxford University Press, pp. 652–654, 1997.

M.D. Shriver et al., "Microsatellite Data Support an Early Population Expansion in Africa," Genome Research, Cold Spring Laboratory Press, 7:586–591, 1997.

X. Guan et al., "A Fast Look–Up Algorithm for Detecting Repetitive DNA Sequences," Pacific Symposium on Biocomputing, pp. 718–719, 1996.

E. Rivals et al., "A First Step Toward Chromosome Analysis by Compression Algorithms," N.G. Bourbakis (editor), First International IEEE Symposium on Intelligence in Neural and Biological Systems, 233239, IEEE Computer Society Press, pp. 1–8, 1995.

S.B. Primrose, "Principles of Genome Analysis, A Guide to Mapping and Sequencing DNA from Different Organisms," Blackwell Science, Cambridge, MA, pp. 25–37, 1995.

M.S. Waterman, "Introduction to Computational Biology," Chapter 11, Chapman & Hall, London, pp. 254–263, 1995.

G. Benson, "A Space Efficient Algorithm for Finding the Best Non–Overlapping Alignment Score," M. Crochemore et al., (editors), Combinatorial Pattern Matching, vol. 807 of Lecture Notes in Computer Science, Springer–Verlag, pp. 1–14, 1994).

G. Benson et al., "A Method for Fast Database Search for All k–Nucleotide Repeats," Nucleic Acids Research, 22, pp. 1–22, 1994.

B. Charlesworth et al., "The Evolutionary Dynamics of Repetitive DNA in Eukaryotes," Nature, vol. 371, pp. 215–220, Sep. 1994.

S.K. Kannan, "An Algorithm for Locating Non–Overlapping Regions of Maximum Alignment Score," Z. Galil et al. (editors), Combinatorial Pattern Matching, vol. 684 of Lecture Notes in Computer Science, Springer–Verlag, pp. 74–86, 1993.

G.M. Landau et al., "An Algorithm for Approximate Tandem Repeats," Z. Galil et al. (editors), Combinatorial Pattern Matching, vol. 684 of Lecture Notes in Computer Science, Springer–Verlag, pp. 120–133, 1993.

A. Milosavljevic et al., "Discovering Simple DNA Sequences by the Algorithmic Significance Method," Cabios, vol. 9, No. 4, pp. 407–411, 1993.

V. Fischetti et al., "Identifying Periodic Occurrences of a Template with Applications to Protein Structure," Z. Galil et al. (editors), Combinatorial Pattern Matching, vol. 644 of Lecture Notes in Computer Science, 7486, Springer–Verlag, pp. 111–120, 1992.

R.M. Karp et al., "Rapid Identification of Repeated Patterns in Strings, Trees and Arrays," Proc. 4th Annual ACM Symp. Theory of Computing, pp. 125–136, 1972.

* cited by examiner

FIG. 5B $h_T$-COMPUTATION ROUTINE: ─╴516

$$h_T(i) = \sum_{P \in \Pi(T)} \sum_{\omega \in L_S(P)} I_{[\omega, \omega + |P| - 1]}(i)$$

$$I_{[a,b]}(x) = \begin{cases} 1 & (\text{if } x \in [a,b]) \\ 0 & (\text{if } x \notin [a,b]) \end{cases}$$

FIG. 5C $f_T$-COMPUTATION ROUTINE: ─╴518

$$f_T(i) = \sum_{j=i-T+1}^{i} h_T(j)$$

FIG. 5D

POTENTIAL TR-CONTAINING-INTERVAL ROUTINE: ─╴520

$I_T^{(j)} = [i_{min}^{(j)}, i_{max}^{(j)}]$ is the j-th interval in s if a) $i_{max}^{(j)}, i_{min}^{(j)} \geq 3T$ b) for all $x \in I_T^{(j)}$, it is $f_T(x) > 0$ c) $f_T(i_{min}^{(j)} - 1) = f_T(i_{max}^{(j)} + 1) = 0$.

THE NUMBER J(T) OF SUCH INTERVAL IN s IS COUNTED.

FIG. 5E

SCORE STATISTICS ROUTINE: ─╴522

```
N=10; M=100;
for(j=0; j<= N-1; j++)
{
    T=Tmin+j(Tmax - Tmin)/(N-1);
    for(i=1; i<=M;i++)
    {
        Randomly choose from s two subsequences
        s1 and s2, of length equal to T;
        score[i]=S(s1,s2); (in percent units)
    }
    K'1 [j]=(1/M)Σ M i=1 score[i];
    K'2 [j]=sqrt[T(1/M)Σ M i=1 (score[i] - K1)2];
}
K1=(1/N)Σ N-1 j=0 K'1 [j];
K2=(1/N)Σ N-1 j=0 K'2 [j];
ξ(p) = erf(p);
```

| RUNTIME [sec] | $W=10$ | $W=11$ | $W=12$ | $W=13$ | $W=14$ | $W=15$ |
|---|---|---|---|---|---|---|
| $\eta=10$ | 8.3 | 16.1 | 36.2 | 94.4 | 223.7 | 552.4 |
| $\eta=5$ | 9.8 | 17.6 | 41.0 | 132.7 | 340.0 | 789.1 |

| NO. REPEATS | $W=10$ | $W=11$ | $W=12$ | $W=13$ | $W=14$ | $W=15$ |
|---|---|---|---|---|---|---|
| $\eta=10$ | 9 | 13 | 21 | 25 | 28 | 28 |
| $\eta=5$ | 9 | 13 | 21 | 26 | 30 | 32 |

TANDEM REPEAT DETECTION USING PATTERN DISCOVERY

CROSS REFERENCE TO RELATED APPLICATION

The present application claims priority to the U.S. provisional patent application identified by Serial No. 60/126,314 filed on Mar. 26, 1999, the disclosure of which is incorporated by reference herein.

FIELD OF THE INVENTION

The present invention generally relates to data sequence processing methodologies and, more particularly, to methods and apparatus for detecting basic repeating subsequences within the data sequences.

BACKGROUND OF THE INVENTION

All living organisms carry the information that allow them to live, in the form of long molecules called DNA (Deoxyribonucleic acid). The structure of these molecules can be idealized as a long chain of four types of chemical components (called nucleotides or bases): adenines, thymines, cytosines and guanines. It is customary to denote these nucleotides by the first letter of its denomination. Thus, we have four types of nucleotides A, T, C, and G. We can say that the set {A,T,C,G} is an alphabet (nothing less than the alphabet of life) in the sense that the order of these letters in the DNA is the genetic text that carries the information needed to build each of our proteins. Proteins are the actual molecules that support and connect the cells of living organisms, mediate communication with the environment and perform most of the chemical reactions needed for living. Proteins are also chain-like molecules which are built out of a set of twenty constituents called amino acids. These twenty amino acids can be conceptualized as an alphabet and the proteins as sentences in this alphabet. An elementary, yet deep, discussion of these alphabets can be found in B. Lewin, "Genes VI," Oxford University Press, 1997. The set of all ordered DNA letters constituting the DNA of an organism is called its genome. The set of all sequences of ordered amino acids (the protein alphabet) of an organism is called its proteome.

Most genomes contain regions that consist of a basic sequence that repeats itself (albeit with slight variations), head to tail, a number of times. These arrangements are called tandem repeats (TR). Both the length of the basic sequence that forms the TR, hereafter called the period of the repeat, and the number of repetitions, hereafter called the copy number, vary from TR to TR within the same genome. The overall amount of repeated genomic material is different in different genomes, ranging from approximately 10% in mammalian genomes to 50% in some arthropods, see, e.g., B. Lewin, "Genes VI," Oxford University Press, 1997.

Even though the functional origin of the repeated sequences is still a matter of debate,. see, e.g., B. Charlesworth, P. Sniegowski and W. Stephan, "The Evolutionary dynamics of repetitive DNA in Eukaryotes," Nature, 371, 215–220, 1994 (the prevailing conjecture being that short repeats might have a structural function), it is clear that their very presence has important consequences during chromosome pairing, allowing for misalignments to occur, and thus causing repeat clusters to be highly polymorphic, see, e.g., B. Lewin, "Genes VI," Oxford University Press, 1997. This polymorphism is used in the forensic technique known as DNA fingerprinting, see. e.g., K. Inman, and N. Rudin, "An Introduction to Forensic DNA Analysis," CRC Press, Boca Raton, Fla., 1997. Longer repeats tend to have a very complex and hierarchical internal structure, whose details might give hints about DNA molecular mechanisms such as misaligned recombination and saltatory replication. For a more extensive discussion of different biological aspects of TR, see, e.g., B. Lewin, "Genes VI," Oxford University Press, 1997; and S. B. Primrose, "Principles of Genome Analysis," Blackwell Science, Cambridge, Mass., 1995.

Despite the fact that the discovery of these surprising repetitive structures took place about 25 years ago, a detailed characterization of the main parameters of the repeats, such as distribution of lengths, distribution of periods, phylogeny of its hierarchical structure, how often they belong to coding as opposed to non-coding regions, etc., is missing. The reasons for this are twofold. On the one hand, only recently enough data to address these questions became available. On the other, and in part due to the first reason, fast algorithms to interrogate the genomes came into existence only recently.

The first attempts to systematically find repeats in sequences dealt with exact repeats, see, e.g., R. M. Karp, R. E. Miller and A. L. Rosenberg, "Rapid identification of repeated patterns in strings, trees and arrays," In Proc. 4th Annu. ACM Symp. Theory of Computing, 125–136, 1972; and A. Milosavljevic and J. Jurka, "Discovering Simple DNA sequences by the Algorithmic Significance Method," Comput. Appl. Biosci., 9, 407–411, 1993. The constraint of exact repetition was relaxed (see, e.g., G. Landau and J. Schmidt, "An algorithm for approximate tandem repeats," Z. Galil, A. Apostolico, M. Crochemore and U. Manber (editors), Combinatorial Pattern Matching, volume 684 of Lecture Notes in Computer Science, 120–133, Springer-Verlag, 1993; S. K. Kannan and E. W. Myers, "An algorithm for locating non-overlapping regions with maximum alignment score," Z. Galil, A. Apostolico, M. Crochemore and U. Manber (editors), Combinatorial Pattern Matching, volume 684 of Lecture Notes in Computer Science, 74–86, Springer-Verlag, 1993; and G. Benson, "A space efficient algorithm for finding the best non-overlapping alignment score," M. Crochemore and D. Gusfield (editors), Combinatorial Pattern Matching, volume 807 of Lecture Notes in Computer Science, 1–14, Springer-Verlag, 1994), where approximate repeats appearing exactly twice either contiguously (the G. Landau and J. Schmidt article) or in a non-overlapping fashion (the S. K. Kannan and E. W. Myers article; and the G. Benson article) were considered. An alternative strategy has also been followed. If the length T of the repeating unit is short enough that all words of that length (see, e.g., E. Rivals and O. Delgrange, "A first step towards chromosome analysis by compression algorithms," N. G. Bourbakis (editor), First International IEEE Symposium on intelligence in Neural and Biological Systems, 233–239, IEEE Computer Society Press, 1995) or all the possible ordered k elements in a window of size T (k<T) (see, e.g., X. Guan and E. C. Uberbacher, "A Fast Look-up Algorithm for Detecting Repetitive DNA Sequences," Pacific Symposium on Biocomputing, 718–719, 1996) can be generated and each used as candidate for the repeating unit, then these candidates can be used as probes and "fitted" to the sequence under interrogation. The same approach can be followed if the repeating unit is given, see, e.g., V. Fischetti, G. Landau, J. Schmidt and P. Sellers, "Identifying periodic occurrences of a template with applications to protein structure," Z. Galil, A. Apostolico, M. Crochemore and U. Manber (editors), Combinatorial Pattern Matching, volume 644 of Lecture Notes in Computer Science, 7486, Springer-Verlag, 1992. In the article. by G. Benson and M. Waterman, "A method for fast database search for all k-nucleotide repeats," Nucelic Acids Research, 22, 4828–4836, 1994, an algorithm that detects TR of a given size was proposed.

All of the above algorithms are practical for a specific range of input parameters. For example, some ofthem are exhaustive algorithms (e.g., the S. K. Kannan and E. W. Myers algorithm; and the G. Benson algorithm), with time complexity being $O(n^2 polylog(n))$ where n is the length of the full sequence, and thus n cannot be too large. This is a serious constraint if entire chromosomes are interrogated (for example, n is about 1,500,000 for chromosome 4 of *S. cerevisiae*). For other algorithms (e.g., the R. M. Karp, R. E. Miller and A. L. Rosenberg algorithm; and the A. Milosavljevic s and J. Jurka algorithm), the constraint of exact repeats is untenable for biological sequences of DNA, where mutations, insertions and deletions constitute important ingredients. Tandem repeats appear in variable copy numbers, and therefore the algorithms that limit the search to only two repeats are too restrictive, see, e.g., the G. Landau and J. Schmidt algorithm. Moreover, the size of the repeating unit can be of a few hundreds, and thus the algorithms that are practical only for short repeats (e.g., the E. Rivals and O. Delgrange algorithm; and the X. Guan and E. C. Uberbacher algorithm) will be useful only in a limited range of sizes. The assumption of the repeat (e.g., the V. Fischetti, G. Landau, J. Schmidt and P. Sellers article), or its length (e.g., the G. Benson and M. Waterman article), being given results in limitations when no a priori knowledge about the repeats is available.

More flexible algorithms that find TR of arbitrary period and copy number have recently been reported, see, e.g., G. Benson, "An Algorithm for Finding Tandem Repeats of Unspecified Pattern Size," S. Istrail, P. Pevzner and M. Waterman (editors), Proc. 2nd Annual ACM Intl. Conference on Comp. Mol. Biol, RECOMB 98, 20–29, 1998; and M.-F. Sagot and E. Myers, "Identifying Satellites in Nucleic Acid Sequences," Proc. 2nd Annual Intl Conference on Comp. Mol. Biol, RECOMB 98, 234–242, 1998. In the M.-F. Sagot and E. Myers approach, the algorithm exhaustively searches for all possible consensus models whose edit distance to the real repeated units is no bigger than an upper bound; it works by extending prefix models. Benson's algorithm (1998) works by finding k-tuples of consecutive characters from the sequence with identical contents (matching k-tuples) at a common distance. A region containing, a sufficiently large number of matching k-tuples is accepted as a TR region if it passes a number of statistical tests based on a probabilistic model.

A cursory comparison of the results reported in the G. Benson article (1998) and the M.-F. Sagot and E. Myers article shows that the sensitivity of both algorithms is different, in that the number of TR reported in both works for the same chromosomes are substantially different. For example, for yeast chromosome 8, no TR model of length greater than 6 was reported in the M.-F. Sagot and E. Myers article, whereas 16 TR of lengths between 10 and 45 were reported in the G. Benson (1998) article. Only TR of size 10 or more were considered in the G. Benson (1998) article, whereas the repeat sizes covered in the M.-F. Sagot and E. Myers article ranged between 2 and 45. It seems that the heuristic algorithm of Benson is very sensitive, being able to detect TR in a wide range of sizes and copy numbers.

However, there is a need for a TR detection algorithm that provides for a considerable improvement in sensitivity, and which eliminates or at least substantially reduces other drawbacks associated with existing approaches.

SUMMARY OF THE INVENTION

The present invention provides for methods and apparatus for detecting repetitive strings in input sequences of letters, characters, or the like. In one aspect of the invention, a computer-implemented method for identifying at least one region of interest in a one-dimensional input sequence comprises the following steps. First, patterns contained in said input sequence are identified. The patterns are then grouped into sets, wherein each pattern in a given set shares a period, where by period we mean the distance between patterns. Then, for at least one set of patterns, the following substeps are performed: (a) for each position P in the input sequence that lies in at least one pattern within the one set of patterns, a data value is generated representing a number of patterns in the set of patterns whose extremes (i.e., first and last characters or letters) flank said position P; a low-pass transformation is applied to the data values for the one set of patterns; subsequent to the transformation of the data values, at least one pair of the transformed data values that satisfy a predetermined criterion is identified. Then, the method provides for identifying the region of interest based upon position in the input sequence corresponding to the pair of data values.

The input sequence may comprise one or more ordered sequences of characters and, in one embodiment, each character of the one or more ordered sequences may be a nucleotide. Further, at least one data value between the pair of data values preferably exceeds a predetermined minimum value. The method may further comprise the step of, upon verifying that the region of interest is a repeating unit, reporting said region of interest to a user or an application.

In another aspect of the invention, a computer-implemented method for identifying regions of interest in a one-dimensional input sequence comprises the following steps. First, a set of repeating units contained in the input sequence is identified, wherein each given repeating unit satisfies at least the following conditions: (a) a first measure of similarity between adjacent repeating units in the set is greater than a first user defined threshold, and (b) the given repeating unit includes at least one unit having a second measure of similarity with any other unit in the set that is a greater than a second user defined threshold. Then, the method provides for reporting positions in the input sequence that are covered by the set of repeating units.

While the inventive algorithm described herein can be used for any sequence of letters, characters, or the like, we shall at times concentrate on its applications to genomics. However, it is to be appreciated that the methodologies of the present invention are not limited to any specific application.

These and other objects, features and advantages of the present invention will become apparent from the following detailed description of illustrative embodiments thereof, which is to be read in connection with the accompanying drawings.

BRIEF DESCRIPTION OF THE DRAWINGS

FIGS. 5A through 5F are flow diagrams of a tandem repeat detection algorithm according to one embodiment of the present invention;

DETAILED DESCRIPTION OF THE INVENTION

Figure 1:
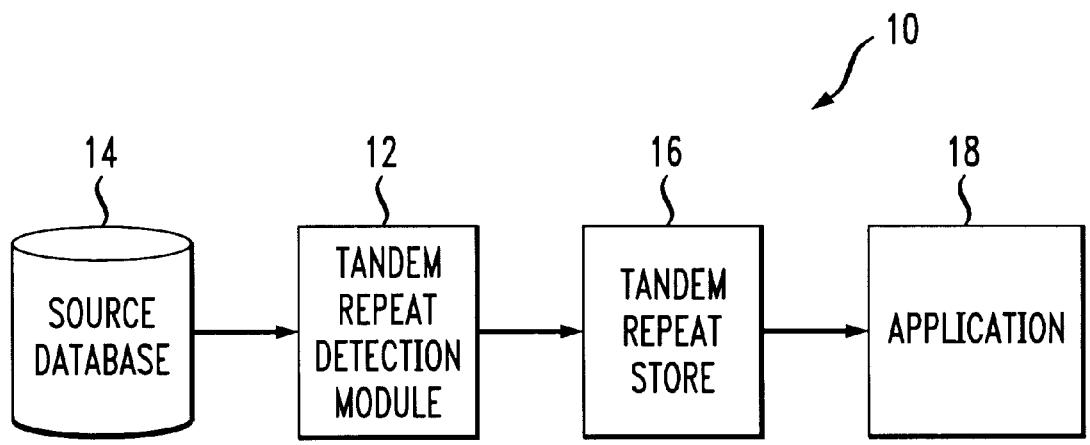
FIG. 1 is a block diagram illustrating a tandem repeat detection system according to one embodiment of the present invention.

Referring initially to FIG. 1, a block diagram of a tandem repeat detection system according to an embodiment of the present invention is shown. The illustrative system 10 includes a tandem repeat detection module 12, a source sequence database. 14 and a tandem repeat (TR) store 16. Also shown is an application 18, which is not necessarily part of the system, but which utilizes one or more of the TR stored in store 16. Generally, the module 12 employs a pattern discovery or detection algorithm, to be explained in detail below, in order to discover tandem repeats from data input from a source database 14. The data sequences in the database may, for example, be in the form of sequences of discrete characters or letters from a fixed alphabet. It is to be appreciated that the source database comprises data sequences from which TR are discovered for use by one or more applications such as, for example, use as polymorphic loci in DNA fingerprinting and parental identification (see, e.g., K. Inman, and N. Rudin, "An Introduction to Forensic DNA Analysis," CRC Press, Boca Raton, Fla., 1997), the study of the effect of TR in disease and treatment (see, e.g., K. Kawakami, K.. Omura, E. Kanehira and Y. Watanabe, "Polymorphic Tandem Repeats in the Thymidilate Synthase Gene is Associated with its Protein Expression in Human Gastrointestinal Cancers," Anticancer Research 19:3249–3252, 1999), use in population genetics and the emerging field of population paleontology (see, e.g., M. D. Shriver, L. Jin, R. E. Ferrell and R. Deka, "Microsatellite Data Support and Early Population Expansion in Africa," Genome Research, 7:586–591, 1997). One can safely predict that further applications are yet to come.

It is to be appreciated that another application which may implement the TR detection methodologies of the invention is DNA or protein sequence homology detection. In such an application, a probe protein sequence may be submitted to a search engine system implementing the invention in order to compare the probe sequence to protein sequences of the database. The database is pre-processed in accordance with the TR detection methodologies of the invention to generate TR. It is to be understood that the probe sequence is compared to the detected TR. The resulting data may have varied applications. For example, it may be used to make a determination as to which sequences in the database the probe sequence is homologous. One of ordinary skill in the art will realize that such a search operation may be greatly improved, for example, from an accuracy and speed standpoint, by pre-processing the sequences in accordance with the methodologies of the invention described herein, prior to the search. Also, another related application is the use of the invention to generate databases of TR. One of ordinary skill in the art will contemplate many other applications given the inventive teachings herein.

Figure 2:
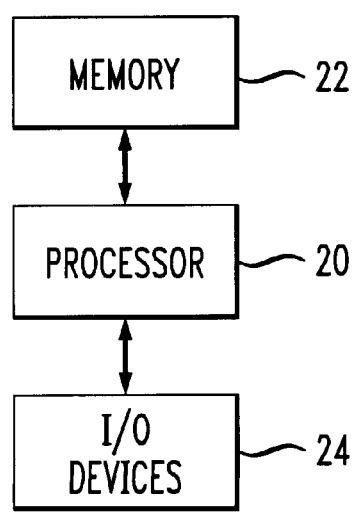
FIG. 2 is a block diagram illustrating a hardware implementation of a tandem repeat detection system according to one embodiment of the present invention.

FIG. 2 is a block diagram of an exemplary hardware implementation of the system 10 of FIG. 1. As shown, the system 10 may be implemented in accordance with a processor 20, a memory 22 and I/O devices 24. It is to be appreciated that the term "processor" as used herein is intended to include any processing device, such as, for example, one that includes a CPU (central processing unit). The term "memory" as used herein is intended to include memory associated with a processor or CPU, such as, for example, RAM, ROM, a fixed memory device (e.g., hard drive), a removable memory device (e.g., diskette), flash memory, etc. In addition, the term "input/output devices" or "I/O devices" as used herein is intended to include, for example, one or more input devices, e.g., keyboard, for entering sequences and/or other data to the processing unit, and/or one or more output devices, e.g., CRT display and/or printer, for presenting detection results and/or other results associated with the processing unit. It is also to be understood that the term "processor" may refer to more than one processing device and that various elements associated with a processing device may be shared by other processing devices. Accordingly, software components including instructions or code for performing the methodologies of the invention, as described herein, may be stored in one or more of the associated memory devices (e.g., ROM, fixed or removable memory) and, when ready to be utilized, loaded in part or in whole (e.g., into RAM) and executed by a CPU.

It is to be appreciated that, in an alternative embodiment, the invention may be implemented in a network-based implementation. That is the user may submit source data sequences (in lieu of a separately stored source database 14) at a remote client computer system, while the TR detection module 12 resides and is executed on a server computer system incommunication with the client via a network such as, for example, the Internet. The network could alternatively be a private network and/or a local network. Thus, a user operating remotely on his client computer system, e.g., a personal computer, laptop and/or some other type of personal processing device, enters data sequences through application software running on the computer system, e.g., web browsing software and/or a graphical user interface associated with the system. The sequences are passed over the network, in a conventional manner, to the server. The server receives the sequences and executes the methodologies of the invention in order to detect tandem repeats in the sequences. The server then returns some or all of the results to the client via the network. It is to be understood that the server may include more than one computer system. That is, one or more of the elements in FIG. 1 may reside on and be executed by their own computer system, e.g., with its own processor, memory and I/O devices.

Given a general description of the elements of the tandem repeat detection system of the invention and various exemplary hardware implementations, the various inventive methodologies will now be explained in detail.

For ease of reference, the remainder of detailed description will be divided into sections as follows: (I) TEIRESIAS; (II) Definition of Tandem Repeats; (III) Detecting Potential TR Regions; (IV) Verification Step; (V) Algorithm Overview; (VI) Scoring Systems and their Statistics; and (VII) Performance.

I. TEIRESIAS

TEIRESIAS is a novel combinatorial algorithm for the discovery of rigid motifs contained in a set of input sequences. Details of the TEIRESIAS algorithm have been described in the literature, e.g., I. Rigoutsos and A. Floratos, Bioinformatics, 14, 55–67, 1998; and I. Rigoutsos and A. Floratos, "Motif discovery without alignment or enumeration," S. Istrail, P. Pevzner and M. Waterman (editors), Proc. 2nd Annual ACM Intl Conference on Comp. Mol. Biol, RECOMB 98, 221–227, 1998, the disclosures of which are incorporated by reference herein. The TEIRESIAS algorithm is also the subject of a U.S. Pat. No. 6,108,666 filed on Feb. 13, 1998, which claims priority to a U.S. provisional application identified by Serial No. 60/049, 461, filed on Jun. 12, 1997, the disclosures of which are incorporated by reference herein. The motifs, or patterns, discovered by TEIRESIAS are guaranteed to be maximal in both length and composition. In order to understand the problem solved by TEIRESIAS and how this is done, we provide a description of the relevant portions of the algorithm below. For the formal presentation of the algorithm, please see the above-incorporated references.

Suppose we have the following string of letters taken from the English alphabet:

ABCD<u>ZZABX</u>EFGHIJK<u>ZZCDX</u>LMNOPQR

A rapid inspection of the previous string allows us to extract a substring that appears more than once. Such substring will be called a "pattern." in the present case, the pattern, is:

ZZ followed by two unspecified letters, followed by X

For brevity, the "followed by an unspecified letter" will be denoted with a dot ".", and thus the previous pattern can be succinctly written as ZZ..X. In the example above, the pattern ZZ..X appeared twice, and thus we say that the "support" of the pattern is 2. In a general string, a pattern might have support bigger than 2, i.e., it might appear more than twice.

In order to restrict the search to patterns that are interesting, it is convenient to impose some constraints to the patterns for which one is searching. One such possible constraint is to demand that if any two letters in a pattern span L characters (e.g., in ZZ..X, the first Z and X span L=5 characters), then there must be a minimum of W letters between (and including) those two. For example, the pattern ZZ..X verifies the constraint L=4, W=2, but it does not verify L=4 W=3. In other words, this is a constraint that determines a minimum density of letters (or a maximum number of dots) within a pattern; we shall call this the density constraint. Patterns satisfying this constraint will be denoted as (L, W)-patterns.

We are also interested in patterns that are as dense and long as possible. If a pattern can be made denser and/or longer without decreasing its support, then we will retain the denser and longer version. The densest and longest patterns will be called "maximal."

Using the above definitions, we can pose the problem addressed by TEIRESIAS in the context of the present application: Given a string of letters as input, and parameters L, W, and K, find all the patterns that: (a) are maximal; (b) verify the density constraint (with the given parameters L and W); and (c) have support at least K.

II. Definition of Tandem Repeats

In accordance with the present invention, an unambiguous definition of TR is provided. Consider the following sentence (written without blanks):

Ideaswiththis<u>trainofthoughttrainofthoughttrainofthought</u> becomefixed where the string <u>trainofthought</u> (underlined each time for the sake of easier identification) is repeated three times in a head to tail way. This is an unambiguous example of what we would like to define as a TR. It's period is 14, i.e., the number of letters in <u>trainofthought</u>. It's copy-number is 3, i.e., the number of consecutive occurrences of <u>trainofthought</u>.

Difficulties arise when, in its different occurrences, the repeating string appears with slight modifications. For example, in the following sentence:

Ideaswiththis<u>trainofthoughttrainofthoughttrainingcough</u>becomefixed the second and third occurrence of <u>trainofthought</u> differ from it slightly, but we still would like to call the previous structure a TR. Our definition of a TR thus depends upon a measure of similarity (also called similarity score or alignment score). There exist many possible measures of similarity and, thus, whether or not a structure is a TR will depend upon the similarity score. For convenience in the present discussion, we shall measure similarity in percentage of identical matches, but other choices of similarity measure may be employed. Some of these other choices are described in Section VI below. However, the present invention is not limited to any particular similarity measure. Thus, our present measure of similarity between two strings (i.e., percentage of identical matches) ranges between 0% (as in the similarity between <u>trainofthought</u> and <u>rabbitsncarrots</u>) through 50% (as in the similarity between <u>trainofthought</u> and <u>tracesofdoughs</u>) up to 100% (as in the similarity between <u>trainofthought</u> and itself).

Our definition of TR comprises two requirements:

(1) The percent similarity between the letter strings that are repeated in a consecutive way (adjacent repeating units) be, on average, greater than a user defined threshold. This threshold will be called $\mu$.

(2) There is at least one repeating substring (the "pivot") whose similarity with any other of the repeating units in the TR is greater than a second threshold that will be called $\alpha$. This second threshold depends on a user defined parameter p (representing the probability that two randomly chosen sequences have percentage similarity equal to or greater than $\alpha$) and on the period T of the TR, see Section VI below.

A TR satisfying these two requirements will be called a (p, $\mu$)-TR. Notice that when a TR has copy number 2, then the previous two definition requirements are indeed the same.

The idea underlying the first condition is that adjacent units should be sufficiently similar "in the mean." This requirement allows for some jump in similarity between adjacent units.

Even if adjacent units are very similar, as we get farther from a given unit, the similarity could degrade. Take the following example:

<u>trainofthoughttracesofdoughdancesofdemons</u>
    (1)          (2)          (3)

Even though the similarity between substring 1 (<u>trainofthought</u>) and 2 (<u>tracesofdoughs</u>) and between substring 2 and 3 (dancesofdemons) is 50%, the similarity between substring 1 and 3 is 0%. If the thresholds $\mu$ and $\alpha$ determined by the first and second requirements in the definition were, e.g., 40%, then the previous example would qualify as a TR of period 14 and copy number 3 if we choose substring 2 as the pivot.

III. Detecting Potential TR Regions

The main heuristics we are going to exploit in our algorithm is that the number of equispaced patterns reported by the TEIRESIAS algorithm is much larger in TR regions than elsewhere in the sequence. To get a quantitative grasp of this fact, let us first consider the simple example of a sequence of length 2,100 letters over the alphabet $\Sigma = \{A, C, G, T\}$. The sequence is assumed random (i.e., the letter at an arbitrary location in the sequence is chosen with equal probability within the letters of the alphabet) except that there is a stretch of length 100 in the middle of the sequence that consists of 5 consecutive exact repetitions of a sequence segment of length 20. If we set the TEIRESIAS parameters to L=10 and W=10 (basically patterns of 10 contiguous letters, or 10-tuples), it can be shown that we should expect an average of two patterns from the random part of the sequence. Thus, most 10-tuples will appear exactly once in the sequence, except, perhaps, for two 10-tuples which will appear twice. However, the 20-tuple motif will be detected as a pattern and will appear 5 times. Furthermore, the length between subsequent occurrences of that 20-tuple will be constant and equal to 20. Thus, the TR region will be that region that contains the highest number of equispaced patterns.

There is an obvious caveat to the previous discussion, which can be easily taken care of. It might happen that for a given sequence, one pattern appears more than twice at equispaced offsets. The likelihood of that event is small, and consequently there will be only a few spurious regions (spurious in the sense of not constituting TR). Thus, each time a TR-candidate region appears, a verification step may be taken to assure that we are indeed in the presence of a TR. Such verification step, as will be explained in Section IV below, will be done on a small set of candidates, most of which verify our definition of TR.

More precisely, let the TEIRESIAS parameters L, W and K, and the sequence s be given. The first step is to use the TEIRESIAS algorithm to find all the.(L, W) maximal patterns $P_j$ of s with support K or more. Let us remind that by (L,W)-pattern, we mean patterns that verify the density constraint discussed in Section I, with parameters L and W. Let $$L_s(P_j) = \{\omega_1^j, \omega_2^j, \ldots, \omega_n^j\}(n = |L_s(P_j)| \geq K)$$

be the offset list of $P_j$, that is the list of sites in the original sequence where the pattern $P_j$ matches s. For example, in the sequence s=ABCD<u>ZZABX</u>EFGHIJK<u>ZZADX</u>LMNOPQRX<u>ZZSTX</u>VW there are two (2,4) patterns: $P_1$=<u>ZZ..X</u> and $P_2$=<u>ZZA.X</u>, with offset lists respectively $L_s(P_1)=\{5,17,30\}$ and $L_s(P_2)=\{5, 17\}$. We shall denote the differences between consecutive offsets by $$T_i^j = \omega_{i+1}^j - \omega_i^j,$$

and by $\Delta_s(P_1)$, the list of differences $\{T_1^j, \ldots, T_{n-1}^j\}$. In the above case, the list of differences is $\Delta_s(P_1)=\{12, 13\}$ and $\Delta_s(P_2)=\{12\}$. For each pattern $P_j$ reported by TEIRESIAS, we shall consider as candidates for TR-periods all those $T_i^j$'s such that $T_{min} \leq T_i^j \leq T_{max}$, where $T_{min,max}$ are the minimum and maximum periods that we are interested in considering, and are input parameters of our algorithlm. For example, in the analysis of the yeast TR as described in Stolovitzky, G., Gao, Y., Floratos, A. and Rigoutsos, I., IBM Technical Report RC21508 (96944), May 21, 1999, the disclosure of which is incorporated by reference herein, $T_{min}$ and $T_{max}$ were chosen as 10 and 300, respectively.

For each T in the interval $[T_{min}, T_{max}]$, we shall call the T-candidate list $\Pi(T)$ to the set of patterns $P_j$ such that there exists at least one difference in the difference list whose value is T. In math terms: there exists at least one i in $\Delta's(P_j)$ with $T_i^j=T$. It is clear that $\Pi(T)$ could be the empty set. In the example above, we have two possible periods: $T_1^1=T_1^2=12$, and $T_2^1=13$. Their respective T-candidate lists are: $\Pi(12)=\{P_1, P_2\}$ and $\Pi(13)=\{P_2\}$ For each T, we define a function $h_T(m)$ as:

$$h_T(m) = \sum_{P \in \Pi(T)} \sum_{\omega \in L_s(P)} I_{[\omega, \omega+|P|-1]}(m) \quad (1)$$

where $|P|$ denotes the length spanned between the first and last letters in the pattern P, and where $I_{[a,b]}(m \in [a, b])=1$ and $I_{[a,b]}(m \notin [a, b])=0$. In equation (1), m ranges from 1 to the length $|s|$ of the sequence s. Because the difference list of each pattern will have a variety of T's, each pattern may belong to more than one T-candidate list.

In words, the value of $h_T$ at location m is equal to the number of patterns in $\Pi(T)$ whose extremes flank the site m. Put differently, site m is in between the first and last letters of exactly $h_T(m)$ patterns in $\Pi(T)$. We explain this below by way of an example. Take the patterns $\pi_1$=<u>A..TT..ACGT</u> and $\pi_2$=<u>TTT.CGT..AA.CG....A</u> that are assumed to be the only patterns in the T-candidate list $\Pi(T)$ that appear in the stretch of sequence (SEQ ID NO: 1) below:

```
                    _____π₂_____
seq: ...GATACAATTTTACGTTAAACCGTCCTATGGTACCA...
              -----π₁-----
         ↑          ↑          ↑
  m =   101        118        127
```

In this example, the left and right extremes of pattern $\pi_1$ (<u>A</u> and <u>T</u>, respectively) clearly flank site m=118. The same is true for pattern $\pi_2$ (whose left and right extremes are <u>T0</u> and <u>A</u> respectively). Thus, for location m=118, we have that $h_T(118)=2$. The sequence location m=127 is a little singular: it is the location where the right extreme of $\pi_2$, <u>A</u>, is. In this case, we shall still say that this site is flanked by pattern $\pi_2$. However, site m=127 is not in between the extremes of pattern $\pi_1$ (i.e., the extremes of pattern $\pi_1$ do not flank site m=127). Therefore, $h_T(m=127)=1$. Finally, site m=101 is not flanked by any pattern belonging to $\Pi(T)$, and thus $h_T(m=101)=0$.

Figure 3:
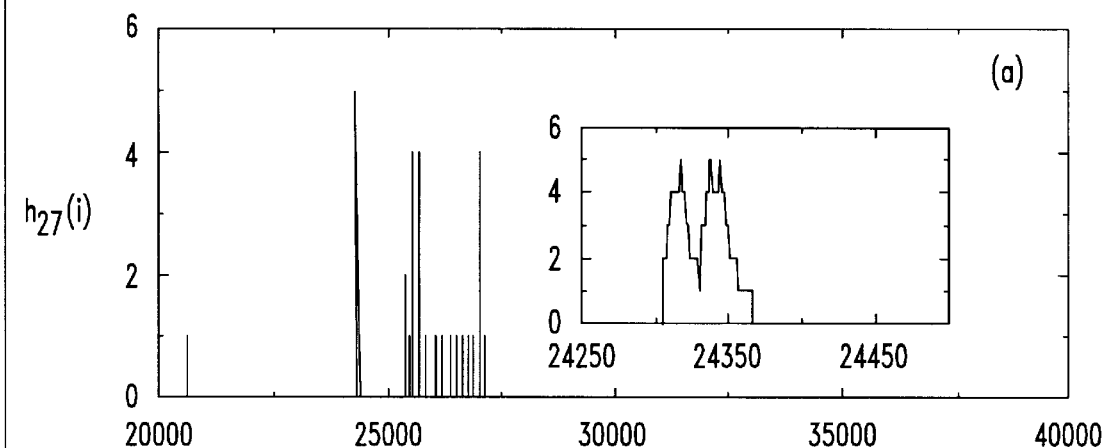
FIGS. 3A and 3B are graphical diagrams illustrating a function $h_T(i)$ used to screen out regions that do not contain tandem repeats, for a period of 27 and a period of 135, respectively, according to one embodiment of a tandem repeat detection algorithm of the present invention.
Figure 3:
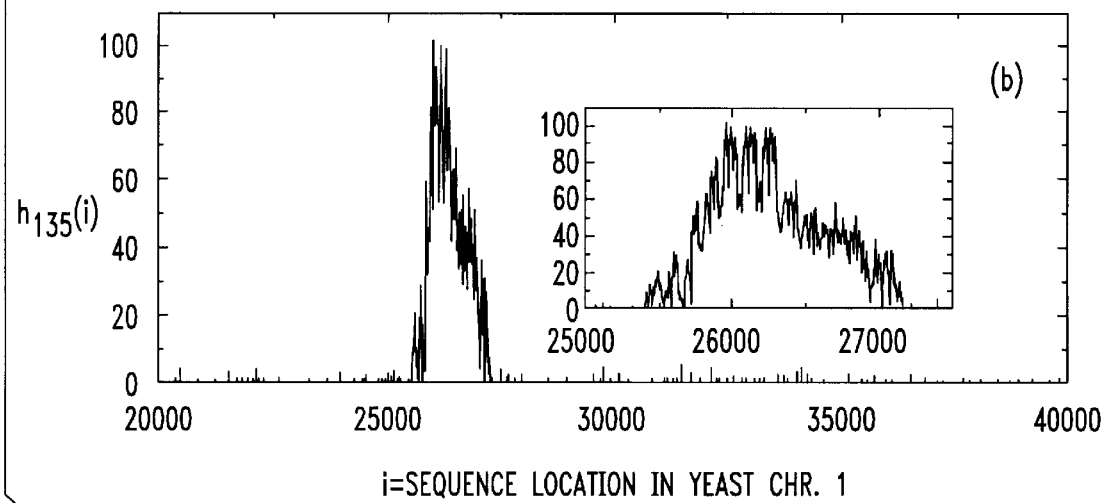

FIG. 3A shows $h_T(i)$ for T=27 and FIG. 3B shows $h_T(i)$ for T=135, for a stretch of size 20,000 in yeast chromosome 1 (data obtained from ftp.ebi.ac.uk, directory pub/databases/yeast). The insets in each figure are enlargements of the highest peak. The parameters chosen for TEIRESIAS were L=10 and W=12. It can be seen in FIG. 3B that there is a clear peak where the patterns accumulate. The fact that $h_{135}$ reaches a value of 102 means that there are 102 patterns voting for period 135 at that location. The situation depicted in FIG. 3A is less clear. In the tallest peak, there are 5 patterns voting for period 27, which is a "marginal" case.

Notice also. that the secondary peaks to the right of the main peak in FIG. 3A are located in the same region where the peak of period 135 is in FIG. 3B. This is an indication that the TR contain some sort of hierarchical structures: within a region with period 135, there are subregions with period 27 (notice that 135=27×5). However, the number of patterns corresponding to period 27 is much smaller than that for period 135.

A third possible behavior for the function $h_T(i)$, not shown in FIGS. 3A and 3B, is that in which not more than one pattern votes for a given period at each location. Typically, those situations do not correspond to TR.

What is the threshold value $\eta$ such that if $h_T(i) \geq \eta$ for some i, we have an appreciable likelihood of having a TR of period T? The answer depends on a number of factors: the values L, W and K that we run TEIRESIAS with, the size of the period T, the number of copies for the TR, and the percentage of mutations between repeating units. The dependence of the threshold $\eta$ on these parameters is rather complex. Here, we take the pragmatic approach of choosing $\eta(T)$ as a compromise between sensitivity and runtime. The approach we shall take is the following: If for some period T, the maximum value reached by $h_T$ is greater than $\eta$, then we proceed to a further verification step, to answer the question of whether or not we are in the presence of a TR that verifies the definition requirements. Alternatively, if $\eta(T)$ is bigger than $h_T(i)$ for all i, we do not process that period any further. It is then clear that if $\eta(T)$ is small, we shall interrogate many regions that will end up not containing any TR, and thus waste time. If we take $\eta(T)$ to be big, we shall process less regions (and thus the program will run faster) but we will miss some TR (false negatives). Experimentation suggests that for L=10 and W=12, $\eta(T)=10$ is a good choice for T>30. For T≤30, we take $\eta(T)=1$. Only if a period T passes the test $h_T \geq \eta(T)$, do we process that period further.

Before going to the verification step, it is convenient to post-process the data contained in the function $h_T$. It would be desirable to have a flag that is bigger than zero in the region where the TR is presumed to be, and zero elsewhere. However, it is clear from the insets of FIGS. 3A and 3B that there need not be patterns covering the full TR region. See, for example, the valley in FIG. 3A, where a depletion of patterns occurs (indicated by the fact that the value of $h_T$ is smaller there). In some cases, those valleys will be deep enough to touch zero, as can be seen in the inset of FIG. 3B. Fortunately, there is (at least) a simple way to overcome this problem. The idea is simply to produce a new function $f_T$ whose value at location i keeps the memory of the number of patterns up to T sites before i. More precisely, we shall compute an additional function corresponding to period T as:

$$f_T(i) = \sum_{j=i-T+1}^{i} h_T(j). \quad (2)$$

Figure 4:
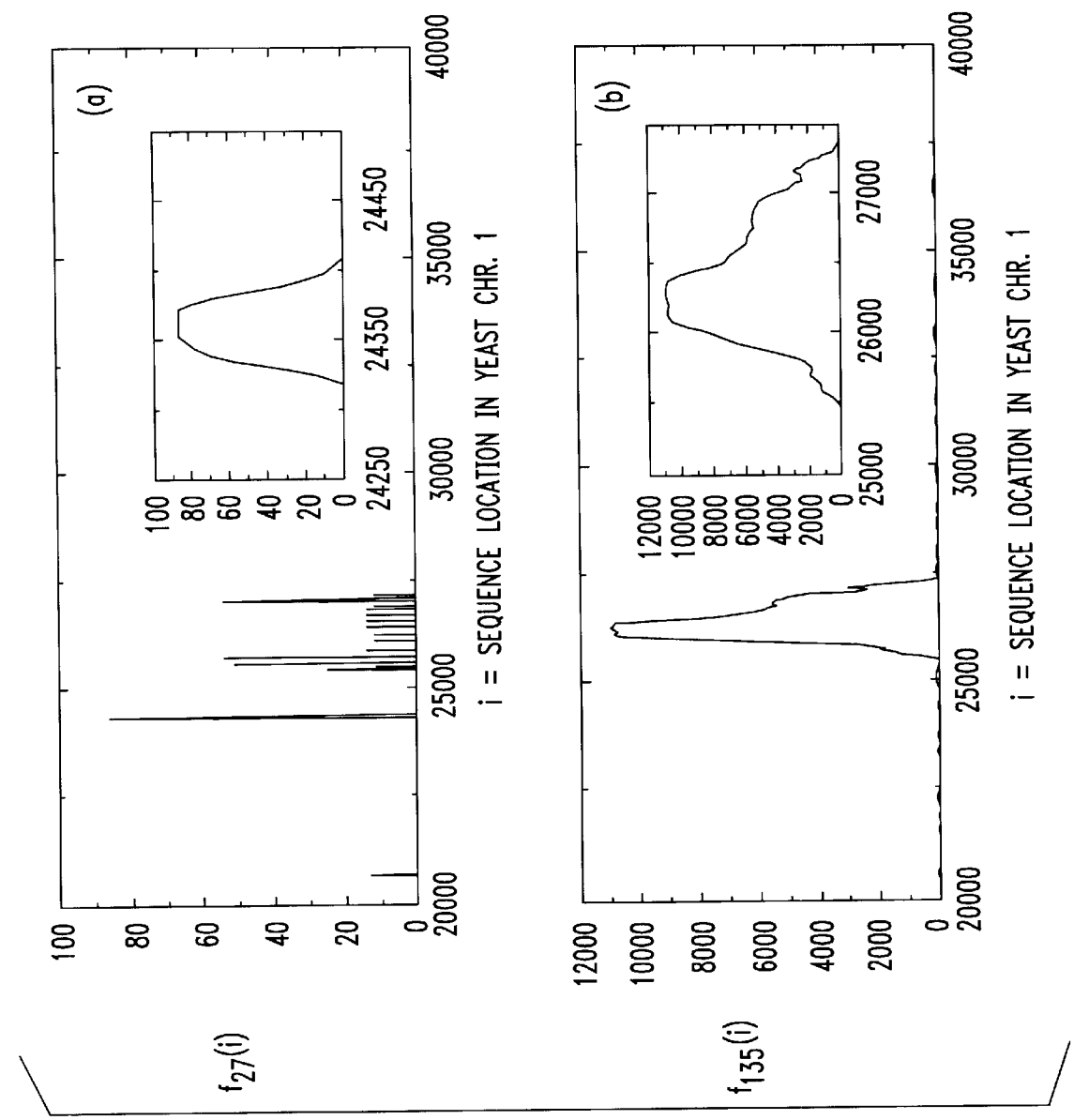
FIGS. 4A and 4B are graphical diagrams illustrating a function $f_T(i)$ used to compute extremes of tandem repeats, for a period of 27 and a period of 135, respectively, according to one embodiment of a tandem repeat detection algorithm of the present invention.

The result of this operation is illustrated in FIGS. 4A and 4B, where everything is the same as in FIGS. 3A and 3B, except that it is $f_T$ instead of $h_T$ that is being plotted. The operation of equation (2) amounts to a low pass filtering of $h_T$. This operation ensures that the flags signaling the regions that are candidates to contain TR (namely the sign of $f$) are strictly positive. To that effect, compare the insets of FIGS. 3A and 3B with those of FIGS. 4A and 4B. The curves in the latter are much smoother than in the former, and are never zero within the region of interest.

The next step is to find those regions for which $f_T$ is strictly positive. For each bump of the kind shown in the insets of FIGS. 4A and 4B, we search for the first values $i_{max}$ and $i_{min}$ to the right and to the left of it such that both $f_T(i_{min})$ and $f_T(i_{max})$ are greater than zero, but $f_T(i_{min}-1)=f_T(i_{max}+1)=0$. If $i_{max}-i_{min}<3T$ (i.e., the support of the considered region spans less than two periods; the 3 appears because of the memory with which $f_T$ was endowed), we do not consider that region any further. However, if $i_{max}-i_{min}>3T$, we proceed to a further verification step (see Section IV below). This is exhaustively done for all periods T in the T-candidate list for which $h_T$ is bigger than $\eta(T)$.

IV. Verification Step

Once we have a region that can potentially contain TR, we have to verify that such region actually contains a TR that satisfies the requirements of our definition.

To be precise, let us choose the parameters $\mu$ and p (with which the second, threshold $\alpha(p, T)$ is computed, see Section VI), required by the definition. The similarity between two sequences $t_1$ and $t_2$ will be denoted by $S(t_1,t_2)$. Suppose we have k consecutive sequences of size T ($k \geq 2$), $t_1, \ldots, t_k$. If k=2, we accept only if $S(t_1, t_2) \geq \max \{\alpha,\mu\}$. If k>2, we proceed in the following way. After having all the k(k-1)/2 pairwise alignment scores, we find the pair for which the score is the highest. If this score is below the score threshold $\alpha$, we decide that the region under consideration does not contain a TR. Otherwise, we choose from the highest scoring pair the element of the pair that is closest to the center of the repeating region and label it as the pivot sequence. We then sweep over the remaining sequences to the right and to the left of the pivot sequence. The extremes of the TR region will be the first sequences to the right and to the left, whose pairwise score with respect to the pivot sequence, along with all the intervening ones, fall above the score threshold $\alpha$. This ensures that the second requirement of the definition is verified. If the array $t_{first}, \ldots, t_{last}$ also satisfies the first requirement, we accept that array as a valid (p, $\mu$)-TR.

V. Algorithm Overview

The pseudo-code based flow chart corresponding to the algorithm described in this section is shown in FIGS. 5A through 5F.

When given a sequence whose TR we wish to detect, we need to provide the following input parameters: L, W, and K (the TEIRESIAS parameters), $T_{min}$ and $T_{max}$ (the minimum and maximum periods we are interested in detecting), $\eta(T)$ (the minimum number of patterns below which we do not bother to explore a region any further), the scoring system, and the parameters $\mu$ and p, with which we shall determine the similarity between elements of the TR.

Figure 5A:
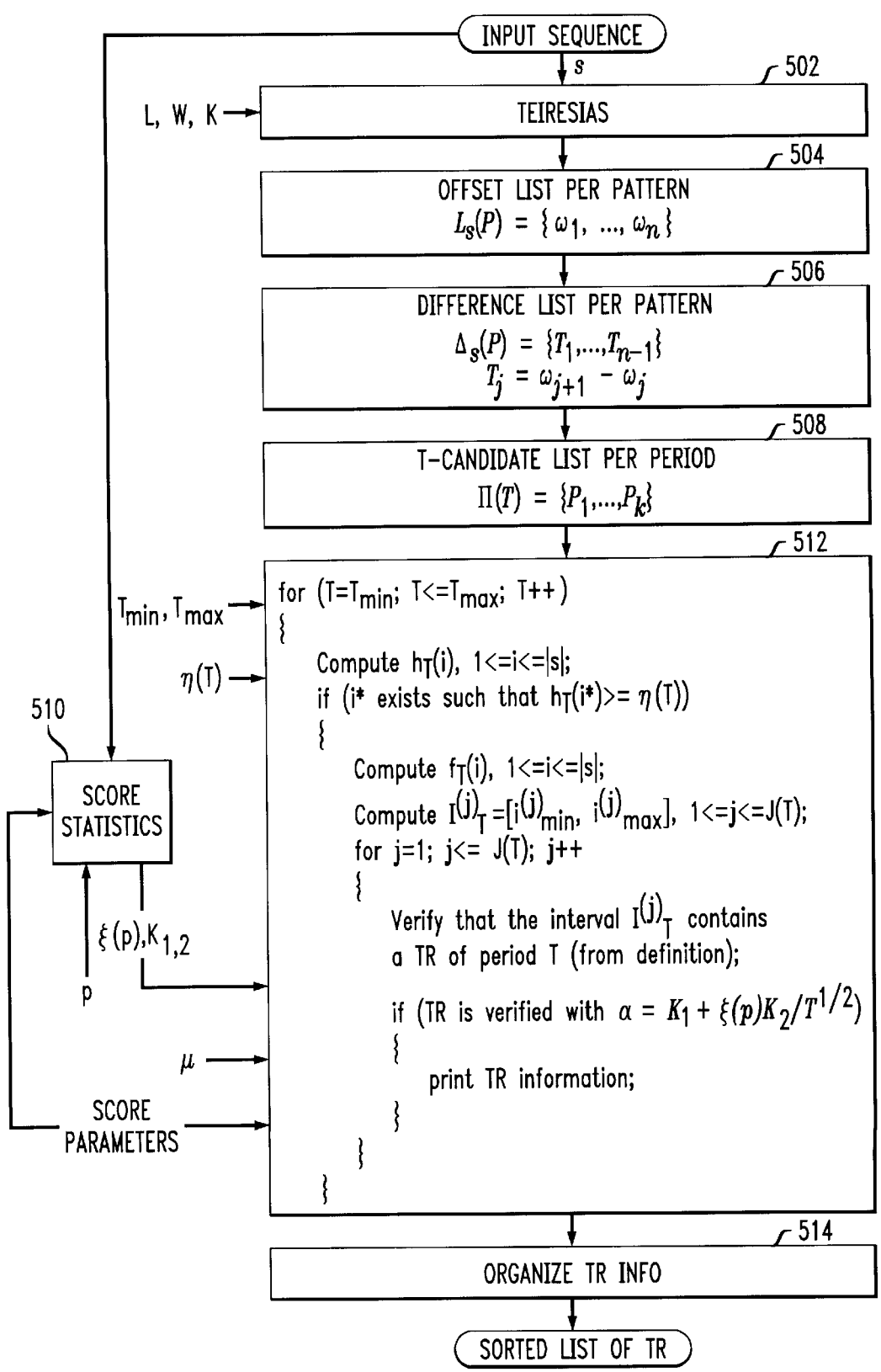
Figure 5F:
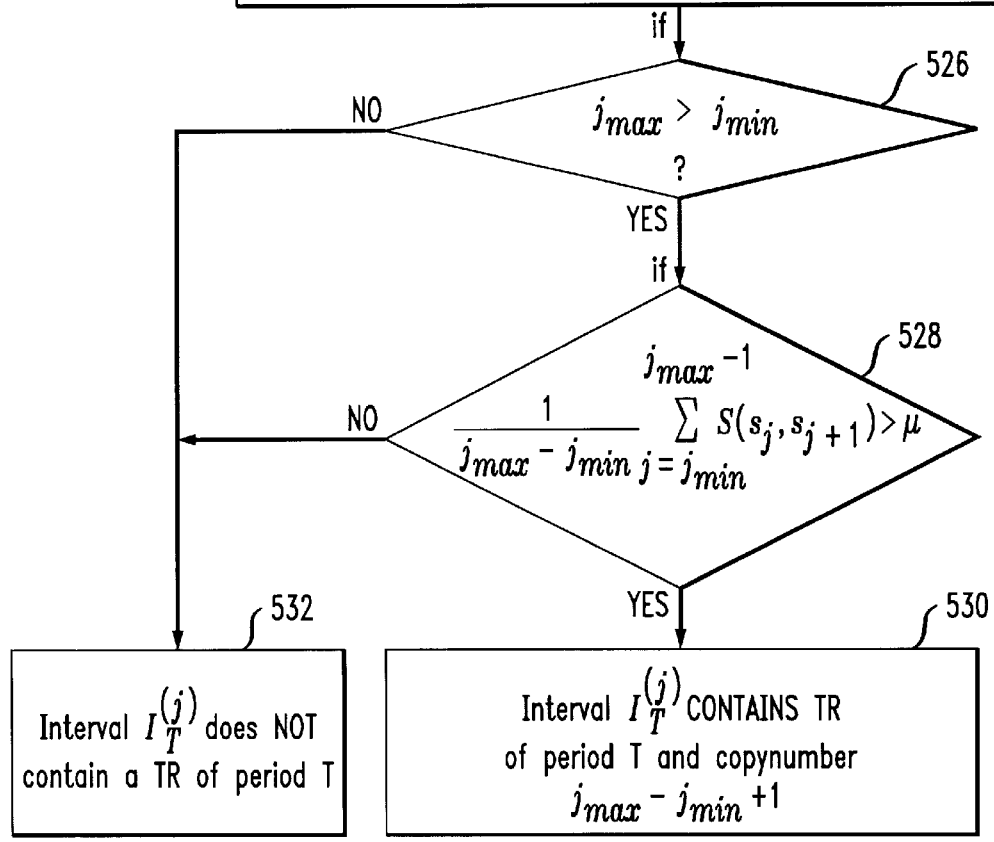

The algorithm gets from TEIRESIAS (step 502) all the maximal (L, W) patterns that appear K times or more in the input sequence. Subsequently, the offset list of these patterns are found (step 504), the difference list is computed (step 506) and the T-candidate list is created (step 508). The main parameters of the score statistics $K_1$ and $K_2$, which relate p and a, are computed from the input sequence (step 510), following the prescriptions detailed in step 522 of FIG. 5E. These parameters, along with the T-candidate lists are fed into the heart of the algorithm depicted in step 512. For each T in the interval $[T_{min},T_{max}]$, whose T-candidate list is non-empty, we compute the function $h_T$ as described in step 516 of FIG. 5B. If $h_T$ gets bigger than $\eta(T)$ at some point, we further compute for that T the function $f_T$ as indicated in step 518 of FIG. 5C. We explore all the connected regions defined in step 520 of FIG. 5D for which $f_T$ is strictly positive and whose length is equal to or greater than 3T (see step 520). If the length of this region is smaller than 3T, we do not consider it further and move to the next region. Otherwise, we check whether there is a subsequence contained in that region that qualifies as a $(p,u)$-TR according to the definition, as indicated in FIG. 5F, and as explained next. In step 524, we explore the given region to check for a set of sequences contained in said region that meet the second requirement of the definition. This is depicted in step 526. If the second requirement is met, we further check that the first requirement is also met, as depicted in step 528. If it is, we claim that the given region contains a TR and specify its copy-number and its period (step 530). If the answer to either of the definition requirement checks (steps 526 and 528) is negative, we claim that the given region does not contain a TR (step 532).

At the output of this process, we sort all the collected information (step 514 of FIG. 5A), and report the following information for all the valid TR: start and stop location of TR, number of copies, length of the repeating unit (period of the repeat), minimum similarity-score between the pivot and the rest of the members of the repeat (which is greater than $\alpha$), average similarity-score between adjacent members of the TR (which is greater than $\mu$).

Examples of the application of this algorithm to genomic data are given in the above-referenced article by Stolovitzky, G., Gao, Y., Floratos, A. and Rigoutsos, I., IBM Technical Report RC21508 (96944), May 21, 1999, where we analyzed in detail the TR in the genome of S. cerevisiae.

VI. Scoring Systems and Their Statistics

When dealing with concrete applications it is necessary to fix a scoring system, and know its statistics. In this section we shall study in some detail a family of global alignment scores (in percent units).

For the results to be presented below, the percent similarity score $S(A, B)$ between sequences A and B, where $A=A_1A_2 \ldots A_T$ and $B=B_1B_2 \ldots B_T$ is computed as:

$$S(A, B) = \max\left\{\frac{1}{T}\sum_{i=1}^{L} s(A_i^*, B_i^*) : \text{all alignments}\right\} \quad (3)$$

where the A*s and B*s that are no insertions and deletions (indels) '−', are equal to their respective A's and B's, and:

$$s(A, A)=1$$

$$s(A, B)=0$$

if A≈B $$s(A, -)=s(-, A)=a$$

if '−' are not terminal gaps $$s(A, -)=s(-, A)=b$$

if '−' are terminal gaps

Let us now discuss the statistics of scores, in order to determine a sensible score threshold $\alpha(p, T)$, used in the second requirement of the TR definition. The statistics of this family of scores will depend upon the choice of a and b. We shall consider two particular cases: $a=b=-\infty$ and $a=-1$, $b=0$.

1) Case $a=b=-\infty$

This case corresponds to the situation in which the alignment is given in advance and there are, no indels, see, e.g., Waterman, M. S., in Chapter 11, pages 254–263, "Introduction to Computational Biology," Chapman & Hall, London, 1995. The scores for this choice of function $s(\cdot,\cdot)$ is simply the percentage of matches of the two sequences. The statistics in this case are well known (see, e.g., the above-referenced Waterman text), but we shall discuss it as it will become of importance for the next choice of a and b.

If two random DNA sequences of length T (generated as T Bernoulli trials in which each outcome can be any of the four events A, C, G and T with probabilities $P_A$, $P_B$, $p_C$ and $P_T$) were to be compared, the number of matches m would follow a binomial distribution:

$$P(m) = C_m^T \rho^m (1-\rho)^{T-m}, \rho = p_A^2 + p_C^2 + p_G^2 + p_T^2, \quad (4)$$

where $C^{T+1}{}_M$ is the binomial coefficient. The expected number of matches is then $(m)=\rho T$, and the variance is $\langle(m-\langle m\rangle)^2\rangle = \rho(1-\rho)T$. Thus, the mean value and standard deviation of the number of matches per unit base, which for this choice of a and b is actually the result of the alignment score, are given by:

$$\mu_T = \left\langle\frac{m}{T}\right\rangle = K_1 \quad (5)$$

$$\sigma_T = \left[\left\langle\left(\frac{m}{T} - \mu_T\right)^2\right\rangle\right]^{1/2} \frac{K_2}{T^{1/2}} \quad (6)$$

where $K_1=\rho$ and $K_2=\sqrt{\rho(1-\rho)}$.

Recall now that the user provides the parameter p (a number between zero and one), whose interpretation is the probability of two subsequences of length T taken randomly from the given sequence to have score equal to or greater than $\alpha$. If we use the normal approximation to the binomial, we have that the score threshold $\alpha(p, T)$ is in this case:

$$\alpha(p, T) = K_1 + \xi(p)\frac{K_2}{T^{1/2}}, \quad (7)$$

where $\xi(p)$ is the inverse of the function (related to the error function):

$$p(\xi) = \frac{1}{\sqrt{2\pi}}\int_\xi^\infty dx \exp\left(-\frac{x^2}{2}\right). \quad (8)$$

If we take $p=0.05$, then $\xi(p)=1.65$.

2) Case $\alpha=-1$, $b=0$

When we allow for a and b to take finite values, the problem makes a leap in difficulty. This is because in this case the alignment is not given, but determined by optimality. In this case, however, we can use a few known theoretical results.

A corollary of Kingman's theorem (see Theorem 11.3 in the above-referenced Waterman text) asserts that for finite a and b, equation (5.) remains valid asymptotically for $T\to\infty$, with $K_1>\pi$. Therefore, equation (5) remains valid at least for T bigger than some value (yet to be determined) below which the asymptotic trend is untenable.

As to the variance, it follows from Steele's theorem (see Theorem 11.6 in the above-referenced Waterman text) that the second centered moment of the global alignment score is bounded by $K'_2T$ (for some constant $K'_2$), and therefore the second centered moment of the global alignment score in 'per base' units verifies:

$$\sigma_T \leq \frac{K'_2}{T^{1/2}} \quad (9)$$

This inequality is close enough to, but not quite the same as, equation (6). We shall see next that equation (6), with an appropriate $K_2$, holds as an excellent approximation for a=−1 and b=0. To do so, we shall resort to numerical experiments to fit the values of $K_1$ and $K_2$ in equations (5) and (6), for the applications to yeast, as mentioned herein.

Figures 6, 7A, 7B:
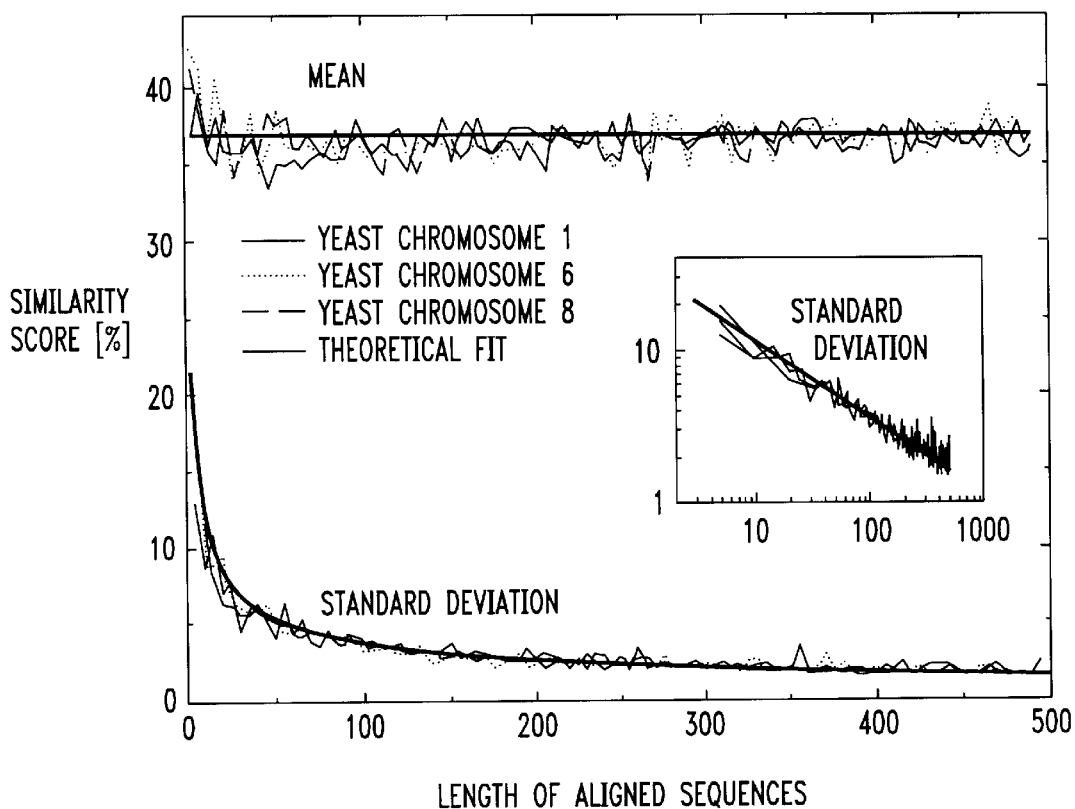
FIG. 6 is a graphical diagram illustrating mean value and standard deviation of global alignment scores between two sequences of different lengths taken at random from chromosomes 1, 6 and 8 of S. cerevisiae.
FIGS. 7A and 7B are tabular diagrams illustrating performance results of a tandem repeat detection algorithm according to one embodiment of the present invention.

In order to have realistic values for $K_1$ and $K_2$, we performed the following numerical experiment. We took independently two randomly chosen subsequences of length T, with 5≦T≦500, from yeast chromosomes 1, 6 and 8. Actually, these samples were taken from those chromosomes, after removing all the poly dA:dT tracts of length bigger than 10. For each chromosome, we computed the scores given by the global alignment when used to align 50 different pairs, and computed the mean and standard deviation of the scores. The results are shown in FIG. 6, where we also plot (thick solid lines) the parameterization given by equations (5) and (6). The, inset, in logarithmic scale, shows that the standard deviation decreases as the power −½ of the period. The best fitted values for $K_1$ and $K_2$ were coincidentally the same for both, and equal to 37%. FIG. 6 shows that our parameterization for $\mu_T$ and $\sigma_T$ fits the experimental data extremely well.

The distribution of these scores (not shown) for large values of T is Gaussian-like, somehow expected from the Central Limit Theorem. Therefore, a sensible score threshold would be the same as in equation (T) with the appropriate values for $K_1$ and $K_2$.

VII. Performance

Both the sensitivity and the runtime performance of the detection algorithm of the invention depend on the set of parameters used in the run. FIGS. 7A and TB show, respectively, instances of the runtime performance in an IBM RS6000 workstation and the number of TR detected by the algorithm, for the following set of parameters: K=2, L=10, 10≦W≦15, $T_{min}$=10, $T_{max}$=300, η(T≦30)=1, η(T>30)=5 or 10, p=0.05 and μ=70%. The sequence under interrogation was the first stretch of 22,000 nucleotides of yeast chromosome 1.

The runtime (FIG. 7A) will typically depend on the parameters L and W for the TEIRESIAS stage of the algorithm, and on the threshold η that is used to determine which periods are going to be subject to further exploration, in the verification stage. FIG. 7A shows that for fixed L=10, the runtime roughly doubles for each increment of W in one unit. To get a rough estimate of the run-times for a yeast chromosome of length L, one has to multiply the previous estimates times L/22,000 (for yeast chromosome 1 this number is 10.5).

FIG. 7B shows the number of repeats detected for the same range of parameters considered in FIG. 7A. It is clear from FIG. 7B, that not much is gained by increasing W above 12, for there is a saturation of the number of TR. Thus, depending on the type of application envisioned, one could sacrifice speed by sensitivity, or vice versa. In the applications to yeast discussed in the above-referenced article Stolovitzky, G., Gao, Y., Floratos, A. and Rigoutsos, I., IBM Technical Report RC21508 (96944), May 21, 1999, a compromise between speed and sensitivity suggested the choice of W=12 and η=10.

The availability of complete genome sequences has allowed in the past few years to develop a feeling for the main features that characterize genomes. One of these features is the structure of sequences that repeat in tandem. In accordance with the present invention, we have described an algorithm which detects TR. A first step in that direction had to be, by necessity, an unambiguous definition of TR. We advanced a definition that is based on the basic intuition of what we expect a TR to be, and devised an algorithm which detects with remarkable sensitivity TR that verify the requirements of our definition.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

---

---

What is claimed is:

1. A computer-implemented method for identifying at least one region of interest in a one-dimensional input sequence, the method comprising the steps of:
   identifying patterns contained in said input sequence;
   grouping said patterns into sets, wherein each pattern in a given set shares a period;
   for at least one set of patterns,
      for each position P in said input sequence that lies in at least one pattern within said one set of patterns, generating a data value representing a number of patterns in said set of patterns whose extremes flank said position P;
      applying a low-pass transformation to said data values for said one set of patterns;
      subsequent to said transformation of said data values, identifying at least one pair of said data values that satisfy a predetermined criterion; and identifying said region of interest based upon position in said input sequence corresponding to said pair of data values.

2. The method of claim 1, wherein the input sequence comprises one or more ordered sequences of characters.

3. The method of claim 2, wherein each character of the one or more ordered sequences is a nucleotide.

4. The method of claim 1, wherein at least one said position P is located within said region of interest, and wherein said data value generated for said position P exceeds a predetermined minimum value.

5. The method of claim 1, further comprising the steps of:

verifying that said region of interest comprises a repeating unit; and reporting said region of interest to a user.

6. The method of claim 1, further comprising the steps of:

verifying that said region of interest comprises a repeating unit; and reporting said region of interest to an application.

7. Apparatus for identifying at least one region of interest in a one-dimensional input sequence, the apparatus comprising:

at least one processor operative to: (i) identify patterns contained in said input sequence; (ii) group said patterns into sets, wherein each pattern in a given set shares a period; (iii) for at least one set of patterns, for each position P in said input sequence that lies in at least one pattern within said one set of patterns, generate a data value representing a number of patterns in said set of patterns whose extremes flank said position P; apply a low-pass transformation to said data values for said one set of patterns; subsequent to said transformation of said data values, identify at least one pair of said data values that satisfy a predetermined criterion; and (iv) identify said region of interest based upon position in said input sequence corresponding to said pair of data values; and a memory, coupled to the at least one processor, operative to store said region of interest.

8. The apparatus of claim 7, wherein the input sequence comprises one or more ordered sequences of characters.

9. The apparatus of claim 8, wherein each character of the one or more ordered sequences is a nucleotide.

10. The apparatus of claim 7, wherein at least one said position P is located within said region of interest, and wherein said data value generated for said position P exceeds a predetermined minimum value.

11. The apparatus of claim 7, wherein the at least one processor is further operative to, verify that said region of interest comprises a repeating unit; and report said region of interest to a user.

12. The apparatus of claim 7, wherein the at least one processor is further operative to, verify that said region of interest comprises a repeating unit; and report said region of interest to an application.

13. An article of manufacture for identifying at least one region of interest in a one-dimensional input sequence, comprising a machine readable medium containing one or more programs which when executed implement the steps of:

identifying patterns contained in said input sequence;

grouping said patterns into sets, wherein each pattern in a given set shares a period;

for at least one set of patterns, for each position P in said input sequence that lies in at least one pattern within said one set of patterns, generating a data value representing a number of patterns in said set of patterns whose extremes flank said position P;

applying a low-pass transformation to said data values for said one set of patterns;

subsequent to said transformation of said data values, identifying at least one pair of said data values that satisfy a predetermined criterion; and identifying said region of interest based upon position in said input sequence corresponding to said pair of data values.

14. The article of claim 13, wherein the input sequence comprises one or more ordered sequences of characters.

15. The article of claim 14, wherein each character of the one or more ordered sequences is a nucleotide.

16. The article of claim 13, wherein at least one said position P is located within said region of interest, and wherein said data value generated for said P exceeds a predetermined minimum value.

17. The article of claim 13, further comprising the steps of:

verifying that said region of interest comprises a repeating unit; and reporting said region of interest to a user.

18. The article of claim 13, fturther comprising the steps of:

verifying that said region of interest comprises a repeating unit; and reporting said region of interest to an application.

19. The method of claim 1 further comprising the step of verifying that said region of interest comprises a repeating unit.

20. The method of claim 19 wherein said verifying step comprises determining:

i) a first measure of similarity between adjacent repeating units is greater than a first user defined threshold, and ii) a second measure of similarity between any other unit is greater than a second user defined threshold.

21. The apparatus of claim 7 wherein said processor is further operative to perform a step of verifying that said region of interest comprises a repeating unit.

22. The method of claim 21 wherein said verifying step comprises determining:

i) a first measure of similarity between adjacent repeating units is greater than a first user defined threshold, and ii) a second measure of similarity between any other repeating unit is greater than a second user defined threshold.

23. The method of claim 13 wherein said one or more programs when executed further implement the step of verifying that said region of interest comprises a repeating unit.

24. The method of claim 23 wherein said verifying step comprises determining:

i) a first measure of similarity between adjacent repeating units is greater than a first user defined threshold, and ii) a second measure of similarity between any other unit is greater than a second user defined threshold.

* * * * *

SEQUENCE LISTING

<160> NUMBER OF SEQ ID NOS: 1

<210> SEQ ID NO 1
<211> LENGTH: 35
<212> TYPE: DNA
<213> ORGANISM: Artificial sequence
<220> FEATURE:
<223> OTHER INFORMATION: This sequence is an example to illustrate the
      invention.

<400> SEQUENCE: 1
gatacaattt tacgttaaac cgtcctatgg tacca                                 35